United States Patent [19]
Bergsma et al.

[11] Patent Number: 5,910,430
[45] Date of Patent: Jun. 8, 1999

[54] ISOLATED NUCLEIC ACID ENCODING G-PROTEIN COUPLED RECEPTOR (HTADX50)

[75] Inventors: Derk J. Bergsma, Berwyn, Pa.; Catherine E. Ellis, Glassboro, N.J.

[73] Assignee: SmithKline Beecham Corporation, Philadelphia, Pa.

[21] Appl. No.: 08/788,750

[22] Filed: Jan. 24, 1997

[51] Int. Cl.$^6$ .............................. C12N 15/12; C12N 15/62
[52] U.S. Cl. ......................... 435/69.1; 435/7.1; 435/7.2; 435/69.7; 435/252.3; 435/320.1; 536/23.4; 536/23.5
[58] Field of Search ........................... 435/7.1, 7.2, 69.1, 435/69.7, 252.3, 320.1; 536/23.4, 23.5, 24.3

[56] References Cited

U.S. PATENT DOCUMENTS 5,466,593  11/1995  Shimomura et al. .................... 435/219

FOREIGN PATENT DOCUMENTS

WO 96 05302  2/1996  WIPO .

OTHER PUBLICATIONS

Sawzdargo et al.; "A Cluster of Four Novel Human G Protein–Coupled Receptor Genes Occurring in Close Proximity to CD22 Gene on Chromosome 19q13.1", Bioch. Biophys. Res. Comm., vol. 239, pp. 543–547 (1997).

Gerszten et al.; "Specificity of the thrombin receptor for agonist peptide is defined by its extracellular surface", Nature, vol. 368, pp. 648–651 (1994).

Oliveira et al.; "A common motif in G–protein–coupled seven transmembrane helix receptors", Journal of Computer–Aided Molecular Design, vol. 7, pp. 649–658 (1993).

Copy of Partial European Search Report of Jul. 1, 1998.

*Primary Examiner*—John Ulm
*Attorney, Agent, or Firm*—Ratner & Prestia; William T. Han; William T. King

[57] ABSTRACT

HTADX50 polypeptides and polynucleotides and methods for producing such polypeptides by recombinant techniques are disclosed. Also disclosed are methods for utilizing HTADX50 polypeptides and polynucleotides in the design of protocols for the treatment of infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others and diagnostic assays for such conditions.

50 Claims, 3 Drawing Sheets

```
  1  GGAATTCCCGGGTCGACCCACGCGTCCGCATGGACAGAAGCAGGGGCTAAAGCTCTGTTC    60
 61  CTCTCTCCTGGAAGCTTGCAGACCTCCCTTCAGAACCAATCCCAAGAAGCCACCTATCCG   120
121  GAACAACACAAGGCAAGCAGCTAGTGTGTGCTTGTGCTTGGAAGAGAGGCCAGGAT       180
181  CAGGTTTGAGGGGAAGGTTCTGGGAGAGCAGGATGTCAGAAACAGCCAAATGGAAGAC     240
241  TCATACCCAGAGACAGAGGACAGAGCTAGTGTGAGGAGCAAGGAGAAACAGCCAGGAAATCAAGGCTG   300
301  GAGAGTGGACAGAGGACAGAGGACCTGGGTGGGCCAGCAAGGTGACACCCAAGTGGA      360
361  AACTGAGTTACCCCGTGAAgAAGATGAGTTCTATTTATGGTCAGAATGCCACGCTCAAGG   420
421  GCCAgTGAAGGCCTGTGGGCTTTTCTGGGCTTTCTCTAAGGTCTTCTAGGGACAAGCCT    480
481  TCCTCCTAAGGCTAGTGCTGTGGTTCTGTTTTTTCTTTTTTTTTTTTTTAgACGGAGTTTTGCTCTTACCGCCCA  540
541  GCTTCCCCTTTTCTTTTTCTTTGCTCAATGGCGCAAATCTTGACTCACTGCAACCTCTGCCTTCCCGGTTCAAGCGA  600
601  GGGTGGAGTGCAAATGGCGCAAATCTTGACTCACTGCAACCTCTGCCTTCCCGGTTCAAGCGA 660
661  TTCTCCTGCCTCAGCCTCCTACCAAGTagCTGGGATTACAGAGGTGCCGCGACTGGAAGAgC 720
                                       M  L  P  D  W  K  S
721  TCCTTGATCCTCATGGCTTAcATCATCATCTTCCTCACTGGCCTCCCTGCCAACCTCCTG   780
      S  L  I  L  M  A  Y  I  I  I  E  F  L  T  G  L  P  A  N  L  L
781  GCCCTGCGGGCCTTTGTGGGGCGGATCCGCCAGCCCCAGCCTGCACCTGTGCACATCCTC   840
      A  L  R  A  F  V  G  R  I  R  Q  P  Q  P  A  P  V  H  I  L
841  CTGCTGAGCCTGACGCTGGCCGACTTCCTCCTCCTGCTGCCCTTCAAGATCATC        900
      L  L  S  L  T  L  A  D  L  L  L  L  L  L  P  F  K  I  I
901  GAGGCTGCGTCGAACTTCCGCTGGTACCTGCCCAAGGTCGTCTGCGCCCTCACGAGTTTT  960
      E  A  A  S  N  F  R  W  Y  L  P  K  V  V  C  A  L  T  S  F
961  GGCTTCTACAGCAGCATCTACTGCAGCACGTGGCTCCTGGCGGGCATCAGCGAGCGC    1020
      G  F  Y  S  S  I  Y  C  S  T  W  L  L  A  G  I  S  I  E  R
```

FIG. 1A

```
1021 TACCTGGGAGTGGCTTTCCCCGTGCAGTACAAGCTCTCCCGCCGGCCTCTGTATGGAGTG 1080
      Y  L  G  V  A  F  P  V  Q  Y  K  L  S  R  R  P  L  Y  G  V

1081 ATTGCAGCTCTGGTGGCCTGGGTTATGTCCTTTGGTCACTGCACCATCGTGATCATCGTT 1140
      I  A  A  L  V  A  W  V  M  S  F  G  H  C  T  I  V  I  I  V

1141 CAATACTTGAACACGACTGAGCAGGTCAGAGAAGTGGCAATGAAATTACCTGCTACGAGAAC 1200
      Q  Y  L  N  T  T  E  Q  V  R  S  G  N  E  I  T  C  Y  E  N

1201 TTCACCGATAACCAGTTGGACGTGGTGCTGCCCGTGCGCCTGGAGCTGTGCCTGGTGCTC 1260
      F  T  D  N  Q  L  D  V  V  L  P  V  R  L  E  L  C  L  V  L

1261 TTCTTCATCCCCATGGCAGTCACCATCTTCTGCTACTGGCGTTTTGTGTGGATCATGCTC 1320
      F  F  I  P  M  A  V  T  I  F  C  Y  W  R  F  V  W  I  M  L

1321 TCCCAGCCCCTTGTGGGGGCCCAGAGGCGGCGCCGAgCCTGGCTGGCTGTGGTGACg 1380
      S  Q  P  L  V  G  A  Q  R  R  R  R  A  V  G  L  A  V  V  T

1381 CTGCTCAATTTCCTGGTGTGCTTCGGACCTTACAACGTGTCCCACCTGGTGGGTATCAC 1440
      L  L  N  F  L  V  C  F  G  P  Y  N  V  S  H  L  V  G  Y  H

1441 CAGAgAAAAAGCCCCTGGTGGGTCAATAgCCGTGGTGTTCAGTTCACTCAACGCCCAGT 1500
      Q  R  K  S  P  W  R  S  I  A  V  V  F  S  S  L  N  A  S

1501 CTGGACCCCCTGCTCTTCTATTTCTCTTCAgTGGTGCGCAGGCATTTGGGAGAgGG 1560
      L  D  P  L  L  F  Y  F  S  S  V  V  R  R  A  F  G  R  G
```

FIG. 1B

```
1561 CTGCAgGTGCTGCGGAATCAGGGCTCCTCCCTGTTGGGACGCAGAGGCAAAGACACAGCA 1620
      L   Q   V   L   R   N   Q   G   S   S   L   L   G   R   R   G   K   D   T   A
1621 GAGGGGACAAATGAGGACAGGGGTGTGGGTCAAGGAGAAGGGATGCCAAGTTCGGACTTC 1680
      E   G   T   N   E   D   R   G   V   G   Q   E   G   M   P   S   S   D   F
1681 ACTACAGAGTAgCAGTTTCCCTGGACCCTTCAGAGGTCGCCTGGGTTACACAGGAGCTGGG 1740
      T   T   E   *
1741 AAGCCTGGGAGAGGCGAGCAGGAAGGCTCCCATCCAGATTCAGAAATCCTTAGACCCAG 1800
1801 CCCAGGACTGCGACTTTGAAAAGGAGCATAAGTGCCTTCACCAGCTCCTCCTTCCTGACTGA 1860
1861 ATTGTCCTACTCAAAGGAGCATAAGTCAGAGATGCACGAAGAGTAGTTAGGTATAGAAG 1920
1921 CACCTGCCGGGTGTGTGAGGTCGGGAGATTGAGAACATCCTGGTCAACATGGGAGGCAGG 1980
1981 TGGATCACTTGAGGTCGGGAGATTGAGAACATGGGAGGAAAACCCGTCTC 2040
2041 TACTAAAAATACAAAAATTAGCTGGGAATCCTTGAACCTGCTATAATCCCAGCTACT 2100
2101 CTGGAGGCTGAGGCAGGAGAATCCTTGAACCCGGAGTTGAAGGTTGCAGTGAGCTGAGA 2160
2161 TCACGCCACTGCACTCCAGCCTGACAGAGCAAGACTCCATTAAAAAAAAAAAAAAAAAAA 2220
2221 GGGCGGCCGCGGCCGCTCTAGAGGATCCCTCGAGGGCCCAAGCTT 2260
```

FIG. 1C

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 2260 base pairs
      (B) TYPE: nucleic acid
      (C) STRANDEDNESS: single
      (D) TOPOLOGY: linear (xi) SEQUENCE DESCRIPTION: SEQ ID NO:1:

```
GGAATTCCCG GGTCGACCCA CGCGTCCGCA TGGACAGAAG CAGGGGCTAA AGCTCTGTTC      60

CTCTCTCCTG GAAGCTTGCA GACCTCCCTT CAGAACCAAT CCCAAGAAGC CACCTATCCG     120

GAACAACACA AGGCAAGGCA GCTAGTGTAG TGCTTGTGCT CTGGGAAGAG AGGCCAGGAT     180

CAGGTTTGAG GGGAAGGTTC TGGGAGACTG GAGGAAGGAT GTCAGAACCA AATGGAAGAC     240

TCATACCCAG AGACAGGAGC TAGTGTGAGG AGCAAGGAAA CAGCCAGGAA ATCAAGGCTG     300

GAGAGTGGAC AGAGGGACAG GACCTGGGTT GGGGCCAGCA AGGGTGACAC CCCAAGTGGA     360

AACTGAGTTA CCCCGTGAAG AAGATGAGTT CTATTTATGG TCAGAATGCC ACGCTCAAGG     420

GCCAGTGAAG GCCTGTGGGC TTTTCTGAAT ATTTCTCTAA GGTCTTCTAG GGACAAGCCT     480

TCCTCCTAAG GCTAGTGCTG GTTCATCCTT CTTCCCCTCC ACCCTCCTCT AAGCCTCCCA     540

GCTTCCCCTT TTCTTTTCTT TTTTTTTTTT TTTAGACGGA GTTTTTGCTC TTACCGCCCA     600
```

```
GGGTGGAGTG CAATGGCGCA ATCTTGACTC ACTGCAACCT CTGCTTCCCG GTTCAAGCGA      660

TTCTCCTGCC TCAGCCTACC AAGTAGCTGG GATTACAGGA TGCTGCCGGA CTGGAAGAGC      720

TCCTTGATCC TCATGGCTTA CATCATCATC TTCCTCACTG GCCTCCCTGC CAACCTCCTG      780

GCCCTGCGGG CCTTTGTGGG GCGGATCCGC CAGCCCCAGC CTGCACCTGT GCACATCCTC      840

CTGCTGAGCC TGACGCTGGC CGACCTCCTC CTGCTGCTGC TGCTGCCCTT CAAGATCATC      900

GAGGCTGCGT CGAACTTCCG CTGGTACCTG CCCAAGGTCG TCTGCGCCCT CACGAGTTTT      960

GGCTTCTACA GCAGCATCTA CTGCAGCACG TGGCTCCTGG CGGGCATCAG CATCGAGCGC     1020

TACCTGGGAG TGGCTTTCCC CGTGCAGTAC AAGCTCTCCC GCCGGCCTCT GTATGGAGTG     1080

ATTGCAGCTC TGGTGGCCTG GGTTATGTCC TTTGGTCACT GCACCATCGT GATCATCGTT     1140

CAATACTTGA ACACGACTGA GCAGGTCAGA AGTGGCAATG AAATTACCTG CTACGAGAAC     1200

TTCACCGATA CCAGTTGGA CGTGGTGCTG CCCGTGCGGG TGGAGCTGTG CCTGGTGCTC      1260

TTCTTCATCC CCATGGCAGT CACCATCTTC TGCTACTGGC GTTTTGTGTG GATCATGCTC     1320

TCCCAGCCCC TTGTGGGGGC CCAGAGGCGG CGCCGAGCCG TGGGGCTGGC TGTGGTGACG     1380

CTGCTCAATT TCCTGGTGTG CTTCGGACCT ACAACGTGT CCCACCTGGT GGGGTATCAC      1440

CAGAGAAAAA GCCCCTGGTG GCGGTCAATA GCCGTGGTGT TCAGTTCACT CAACGCCAGT     1500

CTGGACCCCC TGCTCTTCTA TTTCTCTTCT TCAGTGGTGC GCAGGGCATT TGGGAGAGGG     1560

CTGCAGGTGC TGCGGAATCA GGGCTCCTCC CTGTTGGGAC GCAGAGGCAA AGACACAGCA     1620

GAGGGGACAA ATGAGGACAG GGGTGTGGGT CAAGGAGAAG GGATGCCAAG TTCGGACTTC     1680

ACTACAGAGT AGCAGTTTCC CTGGACCTTC AGAGGTCGCC TGGGTTACAC AGGAGCTGGG     1740

AAGCCTGGGA GAGGCGGAGC AGGAAGGCTC CCATCCAGAT TCAGAAATCC TTAGACCCAG     1800

CCCAGGACTG CGACTTTGAA AAAAATGCCT TTCACCAGCT TGGTATCCCT TCCTGACTGA     1860

ATTGTCCTAC TCAAAGGAGC ATAAGTCAGA GATGCACGAA GAAGTAGTTA GGTATAGAAG     1920

CACCTGCCGG GTGTGGTGGC TCATGCCTAT AATCCCAGAA CTTTGGGAGG CTGAGGCAGG     1980

TGGATCACTT GAGGTCGGGA GATTGAGAAC ATCCTGGTCA ACATGGGAAA ACCCCGTCTC     2040

TACTAAAAAT ACAAAAAAAT TAGCTGGGCA TGGTGGCACA TGCCTATAAT CCCAGCTACT     2100

CTGGAGGCTG AGGCAGGAGA ATCCTTGAAC CCGGGAGTTG GAGGTTGCAG TGAGCTGAGA     2160

TCACGCCACT GCACTCCAGC CTAGCGACAG AGCAAGACTC CATTTAAAAA AAAAAAAAA      2220

GGGCGGCCGC TCTAGAGGAT CCCTCGAGGG GCCCAAGCTT                           2260
```

(2) INFORMATION FOR SEQ ID NO:2:

(i) SEQUENCE CHARACTERISTICS:
        (A) LENGTH: 330 amino acids
        (B) TYPE: amino acid
        (C) STRANDEDNESS: single
        (D) TOPOLOGY: linear (xi) SEQUENCE DESCRIPTION: SEQ ID NO:2:

```
Met Leu Pro Asp Trp Lys Ser Ser Leu Ile Leu Met Ala Tyr Ile Ile
 1               5                  10                  15

Ile Phe Leu Thr Gly Leu Pro Ala Asn Leu Leu Ala Leu Arg Ala Phe
                20                  25                  30

Val Gly Arg Ile Arg Gln Pro Gln Pro Ala Pro Val His Ile Leu Leu
            35                  40                  45

Leu Ser Leu Thr Leu Ala Asp Leu Leu Leu Leu Leu Leu Pro Phe
        50                  55                  60

Lys Ile Ile Glu Ala Ala Ser Asn Phe Arg Trp Tyr Leu Pro Lys Val
```

```
                    65                  70                  75                  80
Val Cys Ala Leu Thr Ser Phe Gly Phe Tyr Ser Ser Ile Tyr Cys Ser
                    85                  90                  95
Thr Trp Leu Leu Ala Gly Ile Ser Ile Glu Arg Tyr Leu Gly Val Ala
                   100                 105                 110
Phe Pro Val Gln Tyr Lys Leu Ser Arg Arg Pro Leu Tyr Gly Val Ile
                   115                 120                 125
Ala Ala Leu Val Ala Trp Val Met Ser Phe Gly His Cys Thr Ile Val
                   130                 135                 140
Ile Ile Val Gln Tyr Leu Asn Thr Thr Glu Gln Val Arg Ser Gly Asn
145                150                 155                 160
Glu Ile Thr Cys Tyr Glu Asn Phe Thr Asp Asn Gln Leu Asp Val Val
                   165                 170                 175
Leu Pro Val Arg Leu Glu Leu Cys Leu Val Leu Phe Phe Ile Pro Met
                   180                 185                 190
Ala Val Thr Ile Phe Cys Tyr Trp Arg Phe Val Trp Ile Met Leu Ser
                   195                 200                 205
Gln Pro Leu Val Gly Ala Gln Arg Arg Arg Ala Val Gly Leu Ala
                   210                 215                 220
Val Val Thr Leu Leu Asn Phe Leu Val Cys Phe Gly Pro Tyr Asn Val
225                230                 235                 240
Ser His Leu Val Gly Tyr His Gln Arg Lys Ser Pro Trp Trp Arg Ser
                   245                 250                 255
Ile Ala Val Val Phe Ser Ser Leu Asn Ala Ser Leu Asp Pro Leu Leu
                   260                 265                 270
Phe Tyr Phe Ser Ser Val Val Arg Arg Ala Phe Gly Arg Gly Leu
                   275                 280                 285
Gln Val Leu Arg Asn Gln Gly Ser Ser Leu Leu Gly Arg Arg Gly Lys
                   290                 295                 300
Asp Thr Ala Glu Gly Thr Asn Glu Asp Arg Gly Val Gly Gln Gly Glu
305                310                 315                 320
Gly Met Pro Ser Ser Asp Phe Thr Thr Glu
                   325                 330

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:3:

GCTTCGGACC TTACAACGTG                                                        20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:4:

CTTCCCAGCT CCTGTGTAAC                                                        20
```

ISOLATED NUCLEIC ACID ENCODING G-PROTEIN COUPLED RECEPTOR (HTADX50)

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to G-protein coupled (7TM) receptor, hereinafter referred to as HTADX50. The invention also relates to inhibiting or activating the action of such polynucleotides and polypeptides.

BACKGROUND OF THE INVENTION

It is well established that many medically significant biological processes are mediated by proteins participating in signal transduction pathways that involve G-proteins and/or second messengers, e.g., cAMP (Lefkowitz, Nature, 1991, 351:353–354). Herein these proteins are referred to as proteins participating in pathways with G-proteins or PPG proteins. Some examples of these proteins include the GPC receptors, such as those for adrenergic agents and dopamine (Kobilka, B. K, et al., Proc. Natl Acad. Sci., USA, 1987, 84:4650; Kobilka, B. K., et al., Science, 1987, 238:650–656; Bunzow, J. R., et al., Nature, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., Science, 1991, 252:802–8).

For example, in one form of signal transduction, the effect of hormone binding is activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane a-helices connected by extracellular or cytoplasmic loops. G-protein coupled receptors include a wide range of biologically active receptors, such as hormone, viral, growth factor and neuroreceptors.

G-protein coupled receptors (otherwise known as 7TM receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structure. The 7 transrembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the b-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said socket being surrounded by hydrophobic residues of the G-protein coupled receptors. The hydrophilic side of each G-protein coupled receptor transmembrane helix is postulated to face inward and form polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc. Rev., 1989, 10:317–331) Different G-protein a-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 transmembrane (7TM) receptors have been successfully introduced onto the market.

This indicates that these receptors have an established, proven history as therapeutic targets. Clearly there is a need for identification and characterization of further receptors which can play a role in preventing, ameliorating or correcting dysfunctions or diseases, including, but not limited to, infections such as bacterial fungal protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

SUMMARY OF THE INVENTION

In one aspect, the invention relates to HTADX50 polypeptides and recombinant materials and methods for their production. Another aspect of the invention relates to methods for using such HTADX50 polypeptides and polynucleotides. Such uses include the treatment of infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. In still another aspect, the invention relates to methods to identify agonists and antagonists using the materials provided by the invention, and treating conditions associated with HTADX50 imbalance with the identified compounds. Yet another aspect of the invention relates to diagnostic assays for detecting diseases associated with inappropriate HTADX50 activity or levels.

BRIEF DESCRIPTION OF THE DRAWINGS

FIGS. 1A, 1B, and 1C shows the nucleotide and deduced amino acid sequence of human HTADX50. SEQ ID NOS: 1 and 2.

DESCRIPTION OF THE INVENTION

Definitions

The following definitions are provided to facilitate understanding of certain terms used frequently herein.

"HTADX50 receptor" refers generally to a polypeptide having the amino acid sequence set forth in SEQ ID NO:2, or of the mature polypeptide encoded by the cDNA insert in the plasmid deposited at the ATCC with Deposit Number ATCC 98283 or an allelic variant thereof.

"Receptor Activity" or "Biological Activity of the Receptor" refers to the metabolic or physiologic function of said HTADX50 receptor including similar activities or improved activities or these activities with decreased undesirable side-effects. Also included are antigenic and immunogenic activities of said HTADX50 receptor. "HTADX50 polypeptides" refers to polypeptides with amino acid sequences sufficiently similar to HTADX50 receptor sequences, preferably exhibiting at least one biological activity of the receptor.

"HTADX50 gene" refers to a polynucleotide having the nucleotide sequence set forth in SEQ ID NO:1 or the nucleotide sequence encoding the mature protein as contained in the cDNA insert in the plasmid deposited at the ATCC with Deposit Number ATCC 98283 or allelic variants thereof and/or their complements.

"HTADX50 polynucleotides" refers to polynucleotides containing a nucleotide sequence which encodes a HTADX50 polypeptide or fragment thereof, or a nucleotide sequence which has at least 60.1% identity to a nucleotide sequence encoding the polypeptide of SEQ ID NO:2 or the corresponding fragment thereof, or a nucleotide sequence which has sufficient identity to a nucleotide sequence contained in SEQ ID NO: 1 or contained in the cDNA insert in the plasmid deposited with the ATCC Deposit Number ATCC 98283 to hybridize under conditions useable for amplification or for use as a probe or marker.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, P., Posttranslational Protein Modifications: Perspectives and Prospects, pgs. 1–12 in POSTTANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymzol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschui, S. F. et al, *J Molec Biol* (1990) 215:403).

Deposited Materials

The invention relates to polypeptides and polynucleotides of a novel HTADX50 receptor, which is related by amino acid sequence identity to thrombin receptor. The invention relates especially to HTADX50 materials having the nucleotide and amino acid sequences set out in FIGS. 1A, 1B, and 1C (SEQ ID NOS: 1 and 2), and to the HTADX50 nucleotide sequences of the human cDNA deposited at the ATCC with Deposit Number ATCC 98283 and amino acid sequence encoded therein.

A deposit containing a human HTADX50 cDNA has been deposited with the American Type Culture Collection (ATCC), 10801 University Boulevard, Manassas, Va. 20110-2209. 20852, USA, on Dec. 20, 1996, and assigned ATCC Deposit Number. ATCC 98283. The deposited material (clone) is DH10B containing pCMVSPORT-1 (Life Technologies, Gaithersburg, Md.) that further contains the full length HTADX50 cDNA, referred to as "pCMVSPORTHTADJX50" upon deposit. The nucleotide sequence of the polynucleotides contained in the deposited material, as well as the amino acid sequence of the polypeptide encoded thereby, are controlling in the event of any conflict with any description of sequences herein.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

Polypeptides of the Invention

The HTADX50 polypeptides of the present invention include the polypeptide of SEQ ID NO:2 (in particular the mature polypeptide) as well as HTADX50 polypeptides and which have at least 80% identity to the polypeptide of SEQ ID NO:2 or the relevant portion and more preferably at least 85% identity, and still more preferably at least 90% identity, and even still more preferably at least 95% identity to SEQ ID NO: 2.

The HTADX50 polypeptides may be in the form of the "mature" protein or may be a part of a larger protein such as a fusion protein. It is often advantageous to include additional amino acid sequence which contains secretory or leader sequences, pro-sequences, sequences which aid in purification such as multiple histidine residues, or additional sequence for stability during recombinant production.

Biologically active fragments of the HTADX50 polypeptides are also included in the invention. A fragment is a polypeptide having an amino acid sequence that entirely is the same as part, but not all, of the amino acid sequence of the aforementioned HTADX50 polypeptides. As with HTADX50 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of HTADX50 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of HTADX50 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate receptor activity, including those with a similar activity or an improved activity, or with a decreased undesirable activity. Also included are those that are antigenic or immunogenic in an animal, especially in a human.

Thus, the polypeptides of the invention include polypeptides having an amino acid sequence at least 80% identical to that of SEQ ID NO:2 or fragments thereof with at least 80% identity to the corresponding fragment of SEQ ID NO:2. Preferably, all of these polypeptides retain the biological activity of the receptor, including antigenic activity. Included in this group are variants of the defined sequence and fragments. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The HTADX50 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to isolated polynucleotides which encode the HTADX50 polypeptides and polynucleotides closely related thereto.

HTADX50 receptor of the invention is structurally related to other proteins of the G-protein coupled receptor, as shown by the results of sequencing the cDNA encoding human HTADX50 in the deposited clone. The cDNA sequence contains an open reading frame encoding a protein of 330 with a deduced molecular weight of 37.1 kDa. HTADX50 of FIGS. 1A, 1B, and 1C (SEQ ID NO:2) has about 28% (using FASTA) identity in 293 amino acid residues with Thrombin Recepton, Cell 64: 1057–1069 (1991). Furthermore, this polypeptide is homologous to Platelet-activating factor Receptor (26.1% in 306 amino acid residues, Biochem. Biophys. Res. Commun. 180(1):1050111 (1991), and the ATP Receptor (24.1% in 307 amino acid residues, FEBS Letters 324(2):219–2). HTADX50 gene of FIGS. 1A, 1B, and 1C (SEQ ID NO: 1) has about 60.1% (using FASTA) identity in 972 nucleotide residues with Human B-cell Receptor (J. Immunol. 150(11):5013–5024 (1993). Furthermore, this receptor is homologous to Interleukin-8 Receptor, 55.8% identity in 303 bp (Genomics 16(1) :248–251 (1993)).

One polynucleotide of the present invention encoding HTADX50 receptor may be obtained using standard cloning and screening, from a cDNA library derived from mRNA in cells of human lung using the expressed sequence tag (EST) analysis (Adams, M. D., et al. *Science* (1991) 252:1651–1656; Adams, M. D. et al., *Nature*, (1992) 355:632–634; Adams, M. D., et al, *Nature* (1995) 377 Supp:3–174). Polynucleotides of the invention can also be obtained from natural sources such as genomic DNA libraries or can be synthesized using well known and commercially available techniques.

Thus, the nucleotide sequence encoding HTADX50 polypeptides may be identical over its entire length to the coding sequence in FIG. 1A, 1B, and 1C (SEQ ID NO: 1), or may be a degenerate form of this nucleotide sequence encoding the polypeptide of SEQ ID NO:2, or may be highly identical to a nucleotide sequence that encodes the polypeptide of SEQ ID NO:2. Preferably, the polynucleotides of the invention contain a nucleotide sequence that is highly identical, at least 60.1% identical, with a nucleotide sequence encoding a HTADX50 polypeptide, or at least 60.1% identical with the encoding nucleotide sequence set forth in FIGS. 1A, and 1B, and 1C (SEQ. ID NO: 1), or at least 60.1% identical to a nucleotide sequence encoding the polypeptide of SEQ ID NO:2.

When the polynucleotides of the invention are used for the recombinant production of HTADX50 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al, *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize MRNA.

Among particularly preferred embodiments of the invention are polynucleotides encoding HTADX50 polypeptides having the amino acid sequence of set out in FIGS. 1A, 1B, and 1C (SEQ ID NO:2) and variants thereof.

Further preferred embodiments are polynucleotides encoding HTADX50 receptor variants that have the amino acid sequence of the HTADX50 receptor of FIGS. 1A, 1B and 1C (SEQ ID NO:2) in which several, 5–10, 1–5, 1–3, 1–2 or 1 amino acid residues are substituted, deleted or added, in any combination.

Further preferred embodiments of the invention are polynucleotides that are at least 60.1% identical over their entire length to a polynucleotide encoding the HTADX50 polypeptide having the amino acid sequence set out in FIGS. 1A, 1B and 1C (SEQ ID NO:2), and polynucleotides which are complementary to such polynucleotides. Most highly preferred are polynucleotides that comprise a region that is at least 60.1% identical over their entire length to a polynucleotide encoding the HTADX50 polypeptide of the human cDNA of the deposited clone and polynucleotides complementary thereto. In this regard, polynucleotides at least 80% identical over their entire length to the same are particularly preferred, and those with at least 90% are especially preferred. Furthermore, those with at least 97% are highly preferred and those with at least 98–99% are most highly preferred, with at least 99% being the most preferred.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are sufficiently identical to a nucleotide sequence contained in SEQ ID NO:1 or to the cDNA insert in the plasmid deposited at the ATCC with Deposit Number ATCC 98283, may be used as hybridization probes for cDNA and genomic DNA, to isolate full-length cDNAs and genomic clones encoding HTADX50 receptor and to isolate cDNA and genomic clones of other genes that have a high sequence similarity to the HTADX50 gene. Such hybridization techniques are known to those of skill in the art. Typically these nucleotide sequences are 70% identical, preferably 80% identical, more preferably 90% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al, BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmid, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HTADX50 polypeptide is to be expressed for use in screening assays, generally, it is preferred that the polypeptide be produced at the surface of the cell. In this event, the cells may be harvested prior to use in the screening assay. If HTADX50 polypeptide is secreted into the medium, the medium can be recovered in order to recover and purify the polypeptide; if produced intracellularly, the cells must first be lysed before the polypeptide is recovered. HTADX50 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of HTADX50 polynucleotides for use as diagnostic reagents. Detection of a mutated form of HTADX50 gene associated with a dysfunction will provide a diagnostic tool that can add to or define a diagnosis of a disease or susceptibility to a disease which results from under-expression, over-expression or altered expression of HTADX50. Individuals carrying mutations in the HTADX50 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled HTADX50 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al., *Proc Natl Acad Sci USA* (1985) 85: 4397–4401.

The diagnostic assays offer a process for diagnosing or determining a susceptibility to infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome through detection of mutation in the HTADX50 gene by the methods described.

In addition, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, can be diagnosed by methods comprising determining from a sample derived from a subject an abnormally decreased or increased level of HTADX50 polypeptide or HTADX50 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an HTADX50 receptor, in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the HTADX50 polypeptides. The term "immunospecific" means that the antibodies have substantial greater affinity for the polypeptides of the invention than their affinity for other related polypeptides in the prior art.

Antibodies generated against the HTADX50 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al, *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against HTADX50 polypeptides may also be employed to treat infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

Vaccines

Another aspect of the invention relates to a method for inducing an immunological response in a mammal which comprises inoculating the mammal with HTADX50 polypeptide, or a fragment thereof, adequate to produce antibody and/or T cell immune response to protect said animal from infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. Yet another aspect of the invention relates to a method of inducing immunological response in a mammal which comprises, delivering HTADX50 gene via a vector directing expression of HTADX50 polypeptide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a HTADX50 polypeptide wherein the composition comprises a HTADX50 polypeptide or HTADX50 gene. The vaccine formulation may further comprise a suitable carrier. Since HTADX50 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The HTADX50 of the present invention may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., Current *Protocols in Immunology* 1(2):Chapter 5 (1991).

HTADX50 proteins are ubiquitous in the mammalian host and are responsible for many biological functions, including many pathologies. Accordingly, it is desirous to find compounds and drugs which stimulate HTADX50 on the one hand and which can inhibit the function of HTADX50 on the other band. In general, agonists are employed for therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome. Antagonists may be employed for a variety of therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium dementia, severe mental retardation and dyskinesias, such as Huntington's disease or Gilles dela Tourett's syndrome.

In general, such screening procedures involve producing appropriate cells which express the receptor polypeptide of the present invention on the surface thereof. Such cells include cells from mammals, yeast, Drosophila or *E. coli*. Cells expressing the receptor (or cell membrane containing the expressed receptor) are then contacted with a test compound to observe binding, or stimulation or inhibition of a functional response.

One screening technique includes the use of cells which express receptor of this invention (for example, transfected CHO cells) in a system which measures extracellular pH or intracellular calcium changes caused by receptor activation. In this technique, compounds may be contacted with cells expressing the receptor polypeptide of the present invention. A second messenger response, e.g., signal transduction, pH changes, or changes in calcium level, is then measured to determine whether the potential compound activates or inhibits the receptor.

Another method involves screening for receptor inhibitors by determining inhibition or stimulation of receptor-mediated cAMP and/or adenylate cyclase accumulation. Such a method involves transfecting a eukaryotic cell with the receptor of this invention to express the receptor on the cell surface. The cell is then exposed to potential antagonists in the presence of the receptor of this invention. The amount of cAMP accumulation is thenmeasured. If the potential antagonist binds the receptor, and thus inhibits receptor binding, the levels of receptor-mediated cAMP, or adenylate cyclase, activity will be reduced or increased.

Another methods for detecting agonists or antagonists for the receptor of the present invention is the yeast based technology as described in U.S. Pat. No. 5,482,835.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed. Standard methods for conducting such screening assays are well understood in the art.

Examples of potential HTADX50 receptor antagonists include antibodies or, in some cases, oligonucleotides or proteins which are closely related to the ligand of the HTADX50 receptor, e.g., a fragment of the ligand, or small molecules which bind to the receptor but do not elicit a response, so that the activity of the receptor is prevented.

Prophylactic and Therapeutic Methods

This invention provides methods of treating an abnormal conditions related to both an excess of and insufficient amounts of HTADX50 receptor activity.

If the activity of HTADX50 receptor is in excess, several approaches are available. One approach comprises administering to a subject an inhibitor compound (antagonist) as hereinabove described along with a pharmaceutically acceptable carrier in an amount effective to inhibit activation by blocking binding of ligands to the HTADX50 receptor, or by inhibiting a second signal, and thereby alleviating the abnormal condition.

In another approach, soluble forms of HTADX50 polypeptides still capable of binding the ligand in competition with endogenous HTADX50 receptor may be administered. Typical embodiments of such competitors comprise fragments of the HTADX50 polypeptide.

In still another approach, expression of the gene encoding endogenous HTADX50 receptor can be inhibited using expression blocking techniques. Known such techniques involve the use of antisense sequences, either internally generated or separately administered. See, for example, O'Connor, *J Neurochem* (1991) 56:560 in Oligodeoxynucleotides as Antisense Inhibitors of Gene Expression, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an under-expression of HTADX50 and its activity, several approaches are also available. One approach comprises administering to a subject a therapeutically effective amount of a compound which activates HTADX50 receptor, i.e., an agonist as described above, in combination with a pharmaceutically acceptable carrier, to thereby alleviate the abnormal condition. Alternatively, gene therapy may be employed to effect the endogenous production of HTADX50 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells ray be administered to a subject for engineering cells in vivo and expression of the polypeptide in vivo. For overview of gene therapy, see Chapter 20, Gene Therapy and other Molecular Genetic-based Therapeutic Approaches, (and references cited therein) in Human Molecular Genetics, T. Strachan and A. P. Read, BIOS Scientific Publishers Ltd (1996).

Formulation and Administration

Peptides, such as the soluble form of HTADX50 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral adminstration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

HTADX50, or Expressed Sequence Tag(EST) 535929 from the Human Genome Science random cDNA database, was first identified from a human activated T-cell cDNA library. By using the BLASTX algorithm with the Non Redundant Protein database this EST was found to possibly encode for a seven transmembrane spanning, G-protein coupled receptor. This EST clone was further sequenced and found to be missing the amino-terminus of the gene. Therefore, the Gene Trapper technology from Life Technologies, Gaithersburg, Md. was utilized to isolate the missing portion of the gene. A 5' primer, 5'GCTTCGGACCTTACAACGTG3'SEQ ID NO:3, and a 3' primer, 5'CTTCCCAGCTCCTGTGTAAC3'SEQ ID NO:4, were designed and synthesized to screen the nine different human plasmid cDNA libraries available from Life Technologies to determine which library contained the cDNA for HTADX50. The human lung was found to contain the cDNA for HTADX50 and the 5' primer discussed previously were used to obtain the full length cDNA for HTADX50 by following the protocol for Gene Trapper exactly.

Example 2

Mammalian Cell Expression

The receptors of the present invention are expressed in either human embryonic kidney 293 (HEK293) cells or adherent dhfr CHO cells. To maximize receptor expression, typically all 5' and 3' untranslated regions (UTRs) are removed from the receptor cDNA prior to insertion into a pCDN or pCDNA3 vector. The cells are transfected with individual receptor cDNAs by lipofectin and selected in the presence of 400 mg/ml G418. After 3 weeks of selection, individual clones are picked and expanded for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectably in about 50% of the G418-resistant clones analyzed.

Example 3

Ligand bank for binding and functional assays.

A bank of over 200 putative receptor ligands has been assembled for screening. The bank comprises: transmitters, hormones and chemokines known to act via a human seven transmembrane (7TW) receptor; naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e. calcium, cAMP, microphysiometer, oocyte electrophysiology, etc, see below) as well as binding assays.

Example 4

Ligand Binding Assays

Ligand binding assays provide a direct method for ascertaining receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

Example 5
Functional Assay in Xenopus Oocytes

Capped RNA transcripts from linearized plasmid templates encoding the receptor cDNAs of the invention are synthesized in vitro with RNA polymerase in accordance with standard procedures. In vitro transcripts are suspended in water at a final concentration of 0.2 mg/ml. Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual Xenopus oocytes in response to agonist exposure. Recordings are made in Ca2+ free Barth's medium at room temperature. The Xenopus system can be used to screen known ligands and tissue/cell extracts for activating ligands.

Example 6
Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

Example 7
Extract/Cell Supernatant Screening

A large number of mama receptors exist for which there remains, as yet, no cognate activating ligand (agonist). Thus, active ligands for these receptors may not be included within the ligands banks as identified to date. Accordingly, the 7TM receptor of the invention is also functionally screened (using calcium, cAMP, microphysiometer, oocyte electrophysiology, etc., functional screens) against tissue extracts to identify natural ligands. Extracts that produce positive functional responses can be sequencially subfractionated until an activating ligand is isolated identified.

Example 8
Calcium and cAMP Functional Assays

7TM receptors which are expressed in HEK 293 cells have been shown to be coupled functionally to activation of PLC and calcium mobilization and/or cAMP stimuation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day>150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP flucuation are tested in vector control cells to determine if the response is unique to the transfected cells expressing receptor.

What is claimed is:

1. An isolated polynucleotide comprising a nucleotide sequence that has at least 80% identity to a polynucleotide sequence encoding the polypeptide having the amino acid sequence of SEQ ID NO:2 over the entire coding region for SEQ ID NO:2 wherein said identity is calculated using FASTA set to obtain the highest order match between the sequences.

2. The isolated polynucleotide of claim 1 wherein said nucleotide sequence is at least 80% identical to the polynucleotide sequence set forth in SEQ ID NO:1 over the entire length of SEQ ID NO:1 and said identity is calculated using FASTA set to obtain the highest order match between the sequences.

3. The isolated polynucleotide of claim 2 wherein said nucleotide sequence is the polynucleotide sequence set forth in SEQ. ID NO:1.

4. The isolated polynucleotide of claim 1 wherein said nucleotide sequence encodes the polypeptide of SEQ ID NO:2.

5. The isolated polynucleotide of claim 1 wherein said nucleotide sequence has at least 90% identity to a polynucleotide sequence encoding the polypeptide of SEQ ID NO:2 over the entire coding region for SEQ ID NO:2 and said identity is calculated using FASTA set to obtain the highest order match between the sequences.

6. The isolated polynucleotide of claim 1 wherein said nucleotide sequence has at least 95% identity to a polynucleotide sequence encoding the polypeptide of SEQ ID NO:2 over the entire coding region for SEQ ID NO:2 and said identity is calculated using FASTA set to obtain the highest order match between the sequences.

7. The isolated polynucleotide of claim 1 wherein said nucleotide sequence has at least 80% identity to the region contained in SEQ ID NO:1 which encodes SEQ ID NO:2 and said identity is calculated using FASTA set to obtain the highest order match between the sequences.

8. The isolated polynucleotide of claim 1 wherein said nucleotide sequence has at least 90% identity to the region contained in SEQ ID NO: 1 which encodes SEQ ID NO:2 and said identity is calculated using FASTA set to obtain the highest order match between the sequences.

9. The isolated polynucleotide of claim 1 wherein said nucleotide sequence has at least 95% identity to the region contained in SEQ ID NO:1 which encodes SEQ ID NO:2 and said identity is calculated using FASTA set to obtain the highest order match between the sequences.

10. The isolated polynucleotide of claim 1 wherein said nucleotide sequence is the region contained in SEQ ID NO:1 which encodes SEQ ID NO:2.

11. The isolated polynucleotide of claim 1 wherein said nucleotide sequence has at least 90% identity to the entire length of SEQ ID NO:1 and said identity is calculated using FASTA set to obtain the highest order match between the sequences.

12. The isolated polynucleotide of claim 1 wherein said nucleotide sequence has at least 95% identity to the entire length of SEQ ID NO:1 and said identity is calculated using FASTA set to obtain the highest order match between the sequences.

13. The isolated polynucleotide of claim 1 wherein said nucleotide sequence is the RNA sequence corresponding to the region contained in SEQ ID NO:1 which encodes SEQ ID NO:2.

14. The isolated polynucleotide of claim 1 wherein said nucleotide sequence is the RNA sequence corresponding to the entire length of SEQ ID NO:1.

15. An isolated polynucleotide comprising a nucleotide sequence encoding at least 15 contiguous amino acids from the amino acid sequence set forth in SEQ ID NO:2.

16. The isolated polynucleotide of claim 15 comprising a nucleotide sequence encoding at least 30 contiguous amino acids from the amino acid sequence set forth in SEQ ID NO:2.

17. The isolated polynucleotide of claim 15 comprising a nucleotide sequence encoding at least 50 contiguous amino acids from the amino acid sequence set forth in SEQ ID NO:2.

18. The isolated polynucleotide of claim 15 comprising a nucleotide sequence encoding at least 100 contiguous amino acids from the amino acid sequence set forth in SEQ ID NO:2.

19. The isolated polynucleotide of claim 15 comprising a nucleotide sequence encoding at least 200 contiguous amino acids from the amino acid sequence set forth in SEQ ID NO:2.

20. The isolated polynucleotide of any one of claims 1, 2, 4 or 19 which is DNA or RNA.

21. An isolated polynucleotide which is complementary to any one of the isolated polynucleotides in claims 1–19.

22. An expression vector comprising a polynucleotide encoding a polypeptide having at least 15 contiguous amino acids from a polypeptide having the amino acid sequence of SEQ ID NO:2.

23. An isolated host cell comprising the expression vector of claim 22.

24. A process for expressing a polypeptide comprising at least 15 contiguous amino acids from the amino acid sequence set forth in SEQ ID NO:2 comprising culturing the host cell of claim 8 under conditions sufficient for the expression of said polypeptide.

25. The process of claim 24 wherein said polypeptide is expressed at the surface of said cell.

26. The process of claim 24 which further includes recovering the polypeptide from the culture.

27. A process for producing a cell which expresses a polypeptide comprising at least 15 contiguous amino acids from the amino acid sequence set forth in SEQ ID NO:2 comprising transforming or transfecting a host cell with the expression vector of claim 22 such that the host cell, under appropriate culture conditions, expresses said polypeptide.

28. Cells produced by the process of claim 27.

29. An expression vector comprising a polynucleotide encoding a polypeptide comprising at least 50 contiguous amino acids from a polypeptide having the amino sequence set forth in SEQ ID NO:2.

30. An isolated host cell comprising the expression vector of claim 29.

31. A process for expressing a polypeptide comprising at least 50 contiguous amino acids from the amino acid sequence set forth in SEQ ID NO:2 comprising culturing the host cell of claim 30 under conditions sufficient for the production of said polypeptide.

32. The process of claim 31 wherein said polypeptide is expressed at the surface of said cell.

33. The process of claim 31 which further includes recovering the polypeptide from the culture.

34. A process for producing a cell which expresses a polypeptide comprising at least 50 contiguous amino acids from the amino acid sequence set forth in SEQ ID NO:2 comprising transforming or transfecting a host cell with the expression vector of claim 29 such that the host cell, under appropriate culture conditions, expresses said polypeptide.

35. Cells produced by the process of claim 34.

36. An expression vector comprising a polynucleotide encoding a polypeptide comprising at least 100 contiguous amino acids from a polypeptide having the amino sequence set forth in SEQ ID NO:2.

37. An isolated host cell comprising the expression vector of claim 36.

38. A process for expressing a polypeptide comprising at least 100 contiguous amino acids from the amino acid sequence set forth in SEQ ID NO:2 comprising culturing the host cell of claim 37 under conditions sufficient for the expression of said polypeptide.

39. The process of claim 38 wherein said polypeptide is expressed at the surface of said cell.

40. The process of claim 38 which further includes recovering the polypeptide from the culture.

41. A process for producing a cell which expresses a polypeptide comprising at least 100 contiguous amino acids from the amino acid sequence set forth in SEQ ID NO:2 comprising transforming or transfecting a host cell with the expression vector of claim 36 such that the host cell, under appropriate culture conditions, express said polypeptide.

42. Cells produced by the process of claim 41.

43. An expression vector comprising a polynucleotide encoding a polypeptide having the amino sequence set forth in SEQ ID NO:2.

44. An isolated host cell comprising the expression vector of claim 43.

45. A process for expressing a polypeptide comprising the amino acid sequence set forth in SEQ ID NO:2 comprising culturing the host cell of claim 44 under conditions sufficient for the expression of said polypeptide.

46. The process of claim 45 wherein said polypeptide is expressed at the surface of said cell.

47. The process of claim 45 which further includes recovering the polypeptide from the culture.

48. A process for producing a cell which expresses a polypeptide comprising the amino acid sequence set forth in SEQ ID NO:2 comprising transforming or transfecting a host cell with the expression vector of claim 43 such that the host cell, under appropriate culture conditions, expresses said polypeptide.

49. Cells produced by the process of claim 48.

50. An isolated polynucleotide comprising a nucleotide sequence selected from the group consisting of:
(a) a nucleotide sequence having at least 80% identity to a nucleotide sequence encoding the same mature polypeptide expressed by the cDNA insert deposited at the ATCC with Deposit Number ATCC 98283; and
(b) a nucleotide sequence complementary to the nucleotide sequence of (a), wherein said identity is calculated using FASTA set to obtain the highest order match between the sequences.

* * * * *